United States Patent
Kelly et al.

(10) Patent No.: US 7,718,837 B2
(45) Date of Patent: May 18, 2010

(54) PROMOTORS FOR CONTROLLING ACIDITY AND PORE SIZE OF ZEOLITE CATALYSTS FOR USE IN ALKYLATION

(75) Inventors: Kevin Kelly, Friendswood, TX (US); James Butler, Friendswood, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 12/145,127

(22) Filed: Jun. 24, 2008

(65) Prior Publication Data
US 2008/0255397 A1    Oct. 16, 2008

Related U.S. Application Data

(63) Continuation of application No. 10/967,881, filed on Oct. 18, 2004, now Pat. No. 7,405,336.

(51) Int. Cl.
*C07C 2/66* (2006.01)

(52) U.S. Cl. ....................................................... 585/467
(58) Field of Classification Search ................. 585/467
See application file for complete search history.

(56) References Cited

U.S. PATENT DOCUMENTS 4,891,458 A * 1/1990 Innes et al. .................. 585/323

\* cited by examiner

*Primary Examiner*—Thuan Dinh Dang
(74) *Attorney, Agent, or Firm*—Tenley R. Krueger

(57) ABSTRACT

A metal-modified alkylation catalyst including a metal/zeolite is provided where the metal is one or two selected from the group consisting of yttrium and a rare earth of the lanthanide series other than cerium. Where two metals are used, one may be Ce or La. The metal-promoted zeolite is useful as a molecular sieve aromatic alkylation catalyst for the production of ethylbenzene by the ethylation of benzene in the liquid phase or critical phase. An alkylation product is produced containing ethylbenzene as a primary product with the attendant production of heavier alkylated by-products of no more than 10-60 wt % of the ethylbenzene.

7 Claims, 1 Drawing Sheet

PROMOTORS FOR CONTROLLING ACIDITY AND PORE SIZE OF ZEOLITE CATALYSTS FOR USE IN ALKYLATION

FIELD OF THE INVENTION

The present invention is related in one non-limiting embodiment to metal-modified alkylation catalysts, and relates more particularly to another non-limiting embodiment to metal/beta zeolite catalysts useful in the alkylation of an aromatic substrate in the liquid phase by a low molecular weight alkylating agent.

BACKGROUND OF THE INVENTION

The alkylation of benzene with ethylene over a molecular sieve catalyst is a well-known procedure for the production of ethylbenzene. Typically, the alkylation reaction is carried out in a multistage reactor involving the interstage injection of ethylene and benzene to produce an output from the reactor that involves a mixture of monoalkyl and polyalkylbenzene. The principal monoalkylbenzene is, of course, the desired ethylbenzene product. Polyalkylbenzenes include diethylbenzene, triethylbenzene, and xylenes.

In many cases, it is desirable to operate the alkylation reactor in conjunction with the operation of a transalkylation reactor in order to produce additional ethylbenzene through the transalkylation reaction of polyethylbenzene with benzene. The alkylation reactor can be connected to the transalkylation reactor in a flow scheme involving one or more intermediate separation stages for the recovery of ethylene, ethylbenzene, and polyethylbenzene.

Transalkylation may also occur in the initial alkylation reactor. In this respect, the injection of ethylene and benzene between stages in the alkylation reactor not only results in additional ethylbenzene production but also promotes transalkylation within the alkylation reactor in which benzene and diethylbenzene react through a disproportionation reaction to produce ethylbenzene.

Various phase conditions may be employed in the alkylation and trans-alkylation reactors. Typically, the transalkylation reactor will be operated under liquid phase conditions, i.e., conditions in which the benzene and polyethylbenzene are in the liquid phase, and the alkylation reactor is operated under gas phase conditions, i.e., pressure and temperature conditions in which the benzene is in the gas phase. However, liquid phase or critical phase conditions can be used where it is desired to minimize the yield of undesirable by-products from the alkylation reactor.

It is a continuing goal of the industry to find and use catalysts that give improved activity and selectivity.

SUMMARY OF THE INVENTION

There is provided, in one form, a molecular sieve catalyst concerning a zeolite promoted with a promoter where the promoter can be one ion selected from the group consisting of yttrium and a rare earth of the lanthanide series other than cerium. Alternatively, the promoter may be two ions where the first ion is yttrium or a rare earth of the lanthanide series other than cerium and the second, different ion is lanthanum, cerium, yttrium or a rare earth of the lanthanide series. It should be understood herein that the term "promoter" also includes a counterion.

There is additionally provided in another non-limiting embodiment a molecular sieve catalyst that involves a zeolite formed with a binder promoted with a promoter that may be one ion which may be yttrium or a rare earth of the lanthanide series other than cerium. Alternatively the promoter may be two ions where the first ion is yttrium or a rare earth of the lanthanide series other than cerium and the second, different ion is lanthanum, cerium, yttrium or a rare earth of the lanthanide series where the promoter ion/aluminum atomic ratio is within the range of from about 0.1 to about 10. Further, the catalyst additionally includes the binder.

In another embodiment, there is provided a process for preparing a molecular sieve catalyst that includes synthesizing a zeolite by hydrothermally digesting a reaction mixture comprising silica, alumina, an alkali metal oxide and an organic templating agent. The synthesized zeolite is treated at least once with an ion-exchange medium to exchange a portion of the active sites in the zeolite with the alkali metal. Further, the ion-exchanged zeolite may be calcined at least once. One or two metals are incorporated into the zeolite system by treating the ion-exchanged zeolite with an ion-exchange medium that includes a metal salt solution to obtain a metal/zeolite. The metal may be one metal that is yttrium or a rare earth of the lanthanide series other than cerium. Alternatively, the metal component may actually be two metals where the first metal is yttrium or a rare earth of the lanthanide series other than cerium and the second, different metal is lanthanum, cerium, yttrium and a rare earth of the lanthanide series. The metal/zeolite is fixed with a binder to produce a mulled metal/zeolite binder mixture. The metal/zeolite binder mixture is pelletized and the resulting pellets are dried.

In a different non-limiting embodiment there is provided a process for alkylation of an aromatic compound that involves supplying an aromatic feedstock into a reaction zone and into contact with a metal-promoted zeolite molecular sieve alkylation catalyst in the reaction zone. The catalyst contains metal in an amount to provide a metal/aluminum atomic ratio within the range of about 0.1 to about 10. The metal may be just one metal that is yttrium or a rare earth of the lanthanide series other than cerium. Alternatively, the metal may be two metals where the first metal yttrium or a rare earth of the lanthanide series other than cerium and the second, different metal is lanthanum, cerium, yttrium or a rare earth of the lanthanide series. A $C_2$-$C_4$ alkylating agent is supplied to the reaction zone in an amount to provide an aromatic compound/alkylating agent mole ratio in the range of about 1 to about 30 inclusive. The reaction zone is operated at temperature and pressure conditions in which the aromatic compound is in the supercritical or liquid phase to cause alkylation of the aromatic compound in the presence of the zeolite alkylation catalyst to give an alkylation product as a primary product with the attendant production of heavier alkylated by-products in a minor amount. The alkylation product is recovered from the reaction zone.

In yet another non-restrictive embodiment there is provided a process for the production of ethylbenzene that includes providing an alkylation reaction zone. The reaction zone contains a metal-promoted zeolite aromatic alkylation catalyst. The metal in the catalyst may be one metal that is yttrium or a rare earth of the lanthanide series other than cerium. Alternatively, the metal may be two metals where the first metal is yttrium or a rare earth of the lanthanide series other than cerium and the second, different metal is lanthanum, cerium, yttrium or a rare earth of the lanthanide series. A feedstock containing at least 20% benzene is co-mingled with a stream containing at least 10% ethylene and supplied to the alkylation reaction zone. The alkylation reaction zone is operated at temperature and pressure conditions in which benzene is in the supercritical phase or liquid phase to cause ethylation of the benzene in the presence of the promoted zeolite alkylation catalyst to produce an alkylation product that includes a mixture of benzene, ethylbenzene, and polyethyl benzene. The alkylation product is recovered from the alkylation reaction zone and the product from the alkylation reaction zone is supplied to a recovery zone for the separation and recovery of ethylbenzene from the alkylation product and the separation and recovery of a polyalkylated aromatic component that includes diethylbenzene. At least a portion of the polyalkylated aromatic component including diethylbenzene in the polyalkylated aromatic component is supplied to a transalkylation reaction zone that contains a molecular sieve transalkylation catalyst. Benzene is supplied to the transalkylation reaction zone, and the transalkylation reaction zone is operated under temperature and pressure conditions to cause disproportionation of the polyalkylated aromatic fraction to produce a disproportionation product having a reduced diethylbenzene content and an enhanced ethylbenzene content.

DETAILED DESCRIPTION OF THE INVENTION

Figure 1:
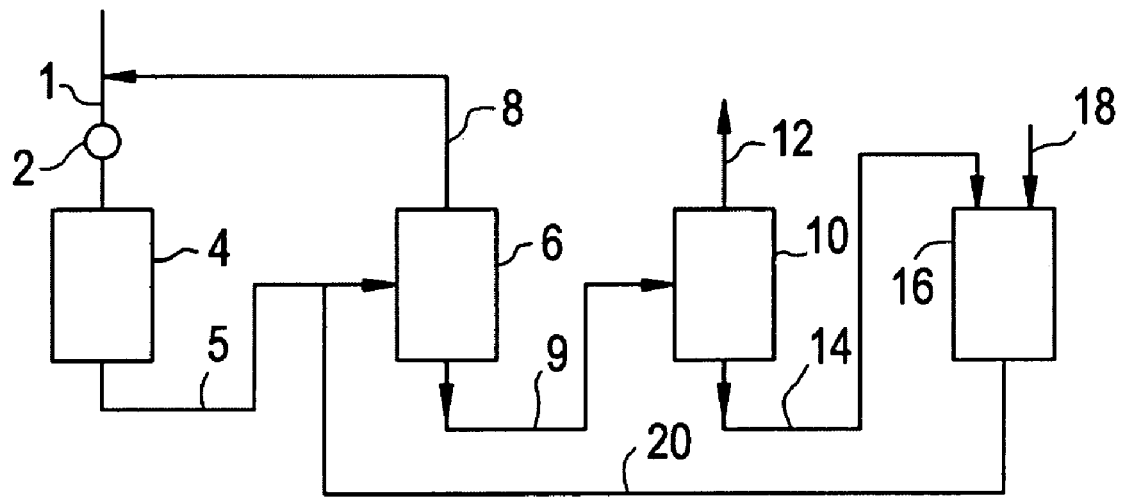
FIG. 1 is an idealized schematic block diagram of an alkylation/trans-alkylation process embodying one non-limiting embodiment of the process.

Cerium has been shown to be superior to lanthanum when used for critical phase alkylation processes. Although both ions possess the same charge, there have been significant differences in activity and selectivity. Attention is respectfully directed to U.S. patent application Ser. No. 10/268,390 filed Oct. 4, 2002 and U.S. patent application Ser. No. 10/678,577 filed Oct. 3, 2003, both of which are incorporated herein in their entirety. Without wishing to be limited to any explanation or theory, it may be that the size of the ion and its acidity could be influential in the alkylation process. Acidity generally increases for these ions as they move to the right along the Periodic Table from lanthanum. Further, those factors could be adjusted with the choice of promoter applied to the zeolite. One important feature is to balance the acidity and the ion size to get optimum results in activity and selectivity. Ion size is thought to affect molecular traffic in and out of the pores of the catalysts.

For example, yttrium (Y) has the same ionic structure as cerium (Ce), although one less orbital is full. It would be a smaller and more electropositive ion than Ce. In addition, other elements in the lanthanide series have the same charge as Ce when ionized, but will be smaller and more electropositive as their position on the Periodic Table moves to the right. One potential promoter might be neodymium (Nd). Its ion is smaller and more electropositive than Ce. Other elements in the lanthanide series may be used to fine-tune their role as promoters. It is expected that only one or two metals will be used in the catalysts, rather than a wide mixture of lanthanides. Thus, in the case where only one promoter is used, the promoter should be yttrium or a member of the lanthanide series other than Ce. In the case where two promoters are used, the first promoter should be yttrium or a member of the lanthanide series other than Ce, and the second promoter should be different than the first, but may be La or Ce or from the same group as the first promoter.

In one non-limiting embodiment, the zeolite has a promoter ion/aluminum atomic ratio ranging from about 0.1/1 to about 2.5/1 relative to the aluminum in the zeolite. (All stated ranges herein are inclusive of the end points unless otherwise noted.) In another non-restrictive embodiment, the ratio of promoter ion to aluminum atomic ratio ranges from about 0.5 to about 1.25.

The molecular sieve catalyst employed in the critical phase alkylation reactor is a zeolite catalyst that can be a conventional zeolite modified by the inclusion of a metal as described below. For the alkylation of this method it is expected that any zeolite may be used. In one non-restrictive embodiment, zeolite Beta is employed. The metal-promoted zeolite catalyst will normally be formulated in extrudate pellets of a size of about ⅛-inch or less (0.32 cm or less), employing a binder such as silica or alumina. In one non-limiting embodiment, the binder is silica, which results in catalysts having somewhat enhanced deactivation and regeneration characteristics than zeolite formulated with a conventional alumina binder. Typical catalyst formulations may include about 20 wt % binder and about 80 wt % molecular sieve. The catalyst employed in a transalkylation reactor normally will take the form of a zeolite Y catalyst, such as zeolite Y or ultra-stable zeolite Y. Various zeolites of the Y and beta types are in themselves well known in the art. For example, zeolite Y is disclosed in U.S. Pat. No. 4,185,040 to Ward, and zeolite beta is disclosed in U.S. Pat. No. 3,308,069 to Wadlinger and U.S. Pat. No. 4,642,226 to Calvert et al., all of which are incorporated by reference herein.

The metal-promoted zeolite employed in the alkylation reactor can be a zeolite of the type described in Wadlinger or Calvert, which has been modified by the inclusion of the metal in the crystalline framework. The metal-promoted zeolite employed can be based on a high silica/alumina ratio zeolite or a ZSM-12 modified zeolite as described. As mentioned, the metal is one or possibly two metals that are from the group of yttrium and a rare earth of the lanthanide series other than cerium. When two metals are used, one of them may be La or Ce.

Basic procedures for the preparation of zeolite are well known to those skilled in the art. Such procedures are disclosed in the aforementioned U.S. Pat. No. 3,308,069 to Wadlinger et al. and U.S. Pat. No. 4,642,226 to Calvert et al. and European Patent Publication No. 159,846 to Reuben, the disclosures of which are incorporated herein by reference in their entirety. The zeolite can be prepared to have a low sodium content, i.e. less than 0.2 wt. % expressed as $Na_2O$ and the sodium content can be further reduced to a value of about 0.02 wt. % by an ion exchange treatment.

As disclosed in the above-referenced U.S. patents to Wadlinger et al., and Calvert et al., zeolite may be produced by the hydrothermal digestion of a reaction mixture comprising silica, alumina, sodium or other alkyl metal oxide, and an organic templating agent. Typical digestion conditions include temperatures ranging from slightly below the boiling point of water at atmospheric pressure to about 170° C. at pressures equal to or greater than the vapor pressure of water at the temperature involved. The reaction mixture is subjected to mild agitation for periods ranging from about one day to several months to achieve the desired degree of crystallization to form the zeolite. Unless steps are taken to minimize the alumina content, the resulting zeolite is normally characterized by a silica to alumina molar ratio (expressed as $SiO_2/Al_2O_3$) of between about 20 and about 500. In an alternate non-limiting embodiment the ratio is between about 50 to about 250.

The zeolite is then subjected to ion exchange with ammonium ions at uncontrolled pH. In one non-limiting embodiment, an aqueous solution of an inorganic ammonium salt, e.g., ammonium nitrate, is employed as the ion-exchange medium. Following the ammonium ion-exchange treatment, the zeolite is filtered, washed and dried, and then calcined at a temperature between about 530° C. and 580° C. for a period of two or more hours.

The zeolite can be characterized by its crystal structure symmetry and by its x-ray diffraction patterns. In a non-limiting example, zeolite beta is a molecular sieve of medium pore size, about 5-6 angstroms, and contains 12-ring channel systems. Zeolite beta is of tetragonal symmetry $P4_122$, where $a=12.7$, $c=26.4$ Å (W. M. Meier and D. H. Olson Butterworth, *Atlas of Zeolite Structure Types*, Heinemann, 1992, p. 58); ZSM-12 is generally characterized by monoclinic symmetry. The pores of zeolite beta are generally circular along the 001 plane with a diameter of about 5.5 angstroms and are elliptical along the 100 plane with diameters of about 6.5 and 7.6 angstroms. Zeolite beta is further described in Higgins et al, "The Framework Topology of Zeolite Beta," *Zeolites*, 1988, Vol. 8, November, pp. 446-452, the entire disclosure of which is incorporated herein by reference.

The procedure disclosed in EP 507,761 A1 to Shamshoum, et al. for incorporation of lanthanum into zeolite beta can be employed to produce the metal promoted zeolite beta used in the present process. Thus, corresponding metal nitrates or other salts may be dissolved in deionized water and then added to a suspension of zeolite beta in deionized water following the protocol disclosed in EP 507,761 A1 for the incorporation of lanthanum into zeolite beta by ion exchange. Following the ion exchange procedure, the metal exchanged zeolite beta can then be filtered from solution washed with deionized water and then dried at a temperature of 110° C. The powdered metal exchanged zeolite beta can then be mulled with an aluminum or silicon binding agent followed by extrusion into pellet form. Other, known procedures may also be used to prepare these zeolites.

The process also involves the liquid phase or critical phase alkylation of benzene over a metal-promoted zeolite alkylation catalyst under conditions to control and desirably minimize the yield of by-products in the alkylation reaction zone. It will be appreciated that although this embodiment is described in terms of alkylating benzene with ethylene as an alkylating agent that the process could also be applied to the alkylation of other aromatic feedstocks using lower alkylating agents such as $C_2$-$C_4$ alkylating agents, with appropriate adjustments.

The feedstock supplied to the alkylation reaction zone comprises benzene and ethylene. Typically, the benzene and ethylene streams will be combined to provide a benzene-ethylene mixture into the reaction zone. The benzene stream, which is mixed with the ethylene either before or after introduction into the reaction zone, should be a relatively pure stream containing only very small amounts of contaminants. In one non-limiting embodiment, the benzene stream may contain at least 90 wt % benzene. Alternatively, the benzene stream will be at least 98 wt % benzene with only trace amounts of such materials as toluene, ethylbenzene, and $C_7$ aliphatic compounds that cannot readily be separated from benzene.

However, it is also possible for the alkylation to be conducted with dilute benzene or dilute ethylene. In such cases, suitable diluents may include, but are not necessarily limited to, ethane, mixed hexanes, mixed butanes, and the like. By the term "dilute" is meant that the ethylene may be present in a ratio with the diluent of about 8/1 or less. The same definition applies with respect to dilute benzene except the ratio of benzene to diluent is less than 8/1. In another non-restrictive version of the process, the reactant may be present in a ratio of about 1/10 or less.

The alkylation reaction may be conducted in the liquid phase at a pressure well above the vapor pressure of the aromatic substrate at the reaction temperature involved to ensure that a liquid phase is maintained in the reaction zone. In the liquid phase, the pressures may range from about 425 to about 600 psia (about 2.9 to about 4.1 MPa), in another non-limiting embodiment from about 450 to about 550 psia (about 3.1 to about 3.8 MPa). The temperature may range from about 175 to about 300° C., alternatively from about 200 to about 250° C. The mole ratio of aromatic compound to alkylating agent may range from about 1 to about 30 in one non-limiting embodiment, and in an alternate, non-restrictive version may range from about 1 to about 25. The liquid phase reaction may be performed in a flooded bed format, a staged reaction format, or other suitable procedure.

The alkylation reaction zone may be also operated under supercritical conditions, that is, pressure and temperature conditions which are above the critical pressure and critical temperature of benzene. Specifically, the temperature in the alkylation zone is at or above about 280° C., and the pressure is at or above about 650 psia (about 4.5 MPa). In another non-limiting embodiment, the temperature in the alkylation reactor will be maintained at an average value within the range of about 280 to about 350° C., alternatively from about 320 to about 380° C. and a pressure within the range of about 650 to about 975 psia (about 4.5 to about 6.7 MPa), in another non-restrictive embodiment from about 550 to about 850 psia (about 3.8 to about 5.9 MPa). If desired, higher alkylation temperatures can be employed since the metal-promoted zeolite retains its structural integrity at temperatures of about 530-540° C. Zeolite which has not been promoted with a metal may lose its structural integrity as the temperature reaches about 500° C. The critical phase alkylation reaction is exothermic with a positive temperature gradient from the inlet to the outlet of the reactor, the temperature increase being determined by the ratio of benzene to ethylene.

The operation of the alkylation reaction zone in the supercritical region enables the alkylation zone to be operated under conditions in which the benzene-ethylene mole ratio can be maintained at relatively low levels, usually somewhat lower than the benzene-ethylene mole ratio encountered when the alkylation reaction zone is operated under liquid phase conditions. In most cases, the benzene-ethylene mole ratio will be within the range of about 1-15. In another non-limiting embodiment, the benzene mole ratio will be maintained during at least part of a cycle of operation at a level within the lower end of this range, specifically, at a benzene-ethylene mole ratio of less than about 10. A benzene-ethylene mole ratio within the range of 3-8 may be employed with adequate cooling of the reactor. Thus, operation in the supercritical phase offers the advantages of gas phase alkylation in which the benzene-ethylene ratio can be kept low but without the problems associated with by-product formation, specifically xylene formation, often encountered in gas-phase alkylation. At the same time, operation in the super critical phase offers the advantages accruing to liquid phase alkylation in which the by-product yield is controlled to low levels. The pressures required for operation in the super critical phase are not substantially greater than those required in liquid phase alkylation, and the benzene in the supercritical phase functions as a solvent to keep the zeolite catalyst clean and to retard coking leading to deactivation of the catalyst. However, it should be understood that liquid phase conditions can be used with this process.

As indicated by the experimental work described later, the metal-promoted zeolite enables super critical phase alkylation to be carried out with by-products that are expected to be substantially less than the corresponding by-products produced with super critical phase alkylation employing lanthanum-promoted beta zeolite of similar or greater content. Thus, the alkylation reaction zone can be operated at super critical phase temperature and pressure conditions to provide a composite by-product yield of propylbenzene and butylbenzene which is less than the corresponding composite by-product yield of propylbenzene and butylbenzene for a corresponding beta zeolite catalyst promoted with lanthanum at a lanthanum/beta atomic ratio at least as great as the metal/aluminum atomic ratio of the metal-promoted zeolite. In one non-limiting embodiment, the alkylation reaction zone is operated at temperature and pressure conditions to provide a composite product yield of propylbenzene and butylbenzene which is no more than one-half of the corresponding composite by-product yield of propylbenzene and butylbenzene produced with the lanthanum-promoted zeolite beta. In another non-limiting embodiment, the composite product yield of propylbenzene and butylbenzene is no more than that of the corresponding composite by-product yield of propylbenzene and butylbenzene produced with the lanthanum-promoted zeolite beta. The same advantages are expected to be present when the reaction is conducted under liquid phase conditions.

Turning now to FIG. 1, there is illustrated a schematic block diagram of an alkylation/transalkylation process employing one or more of the innovations described herein. As shown in FIG. 1, a product stream comprising a mixture of ethylene and benzene in a mole ratio of benzene to ethylene of about 1 to 30 is supplied via line 1 through a heat exchanger 2 to an alkylation reaction zone 4. Alkylation zone 4 in one non-limiting embodiment comprises one or more multi-stage reactors having a plurality of series-connected catalyst beds containing a metal-modified zeolite alkylation catalyst as described herein. The alkylation zone 4 is operated at temperature and pressure conditions to maintain the alkylation reaction in the liquid or supercritical phase, i.e. the benzene is in the liquid or supercritical state, and at a feed rate to provide a space velocity enhancing diethylbenzene production while retarding by-products production. In another non-limiting embodiment, the space velocity of the benzene feed stream will be within the range of 1-150 hrs$^{-1}$ LHSV per bed. The output from the alkylation reactor 4 is supplied via line 5 to an intermediate benzene separation zone 6 that may take the form of one or more distillation columns. Benzene is recovered through line 8 and recycled through line 1 to the alkylation reactor 4. The bottoms fraction from the benzene separation zone 6, which includes ethylbenzene and polyalkylated benzenes including polyethylbenzene, is supplied via line 9 to an ethylbenzene separation zone 10. The ethylbenzene separation zone 10 may likewise involve one or more sequentially connected distillation columns. The ethylbenzene is recovered through line 12 and applied for any suitable purpose, such as in the production of vinyl benzene. The bottoms fraction from the ethylbenzene separation zone 10, which comprises polyethylbenzene, principally diethylbenzene, is supplied via line 14 to a transalkylation reactor 16. Benzene is supplied to the transalkylation reaction zone through line 18. The transalkylation reactor 16, which in one non-limiting embodiment is operated under liquid phase conditions, contains a molecular sieve catalyst, in one non-limiting embodiment zeolite-Y, which has a somewhat larger pore size than the metal-modified zeolite used in the reaction alkylation zone. The output from the transalkylation reaction zone 16 is recycled via line 20 to the benzene separation zone 6.

It will be appreciated that the process herein may be used in conjunction with parallel-connected alkylation and transalkylation reactors with multi-stage recovery zones for separating and recycling of components. Such systems are described in U.S. Patent Application No. 2004/0068151 to Kevin P. Kelly, et al., which is incorporated herein by reference in its entirety. The catalysts and processes will now be further discussed with respect to certain more specific Examples which are provided merely to further illustrate the innovations previously discussed and not to limit them in any way.

EXAMPLE 1

A beta zeolite catalyst would be prepared by employing a multiple ion exchange and calcinations procedures as described previously. The beta zeolite may have a silica/aluminum ratio of about 25 (within the range of about 20 to 500), and contain tetraethylammonium hydroxide as a retained templating agent, and may have an initial surface area of 210 m$^2$/g and a sodium content of about 0.5 to 1% Na$_2$O after calcination. The initial ammonium ion exchange treatment may be done by submersing the calcined zeolite catalyst in an aqueous solution of ammonium nitrate having a normality of 2 at a zeolite to ammonium nitrate ratio of about 2:3. The zeolite beta may be submersed in the ion exchange medium under mild agitation at 85° C. for a period of two hours. The beta zeolite may then be filtered and dried. The dried powder may be calcined at programmable temperature to a maximum of 570° C. convert the zeolite to the hydrogen form. This calcined powder would then be ion-exchanged with ammonium ions in a similar manner as described above. Alternatively, it should be appreciated that commercial zeolites may be acquired to make the catalysts.

The metal as defined herein may then be incorporated into the zeolite system by an ion exchange method. In a non-restrictive instance, 80 grams of anhydrous NH$_4$/beta zeolite may be suspended in deionized water. A salt solution of metal nitrate may be prepared by dissolving 1.247 grams of M(NO$_3$)$_3$ in deionized water. This salt solution may be slowly added to the zeolite suspension at a temperature of about 90° C. The exchange may be continued for about 3 hours. The metal exchanged zeolite may be filtered, washed and dried at 110° C. The chemical analysis of this powder form (metal/NH$_4$ beta-zeolite could be as given below in Table I, and may show a metal content of about 0.1 wt %.

TABLE I

Chemical Analysis (anhydrous basis) of Metal/beta Zeolite

| | Wt % | | | | | |
|---|---|---|---|---|---|---|
| Sample | Si | Al | Metal | Na* | K* | SiO$_2$/Al$_2$O$_3$ |
| Metal/NH$_4$ beta | 43.2 | 2.7 | 0.12 | 0 | 0 | 30.9 |

* < 0.01%

The powdered metal/beta zeolite (e.g. 66.7 g, anhydrous basis) may be mulled with nitric acid-treated alumina (for instance 21.9 g, anhydrous basis) and extruded into $\frac{1}{16}$ inch pellets. (0.16 cm). The resulting extruded zeolite pellets may then be calcined in an oven under air in a programmed temperature, up to a maximum of about 530° C. The metal/NH$_4$ beta catalyst could thus be converted into a metal oxide/H-beta catalyst as the ammonia evolved [NH$^4$→NH$^{3+}$H$^+$] during calcinations of the extrudates at 530° C. The final catalyst may have the physical properties given in Table II.

TABLE II

Properties Expected for an Example I Catalyst

| | |
|---|---|
| Surface Area | 609.1 m$^2$/g |
| Micropore Area | 325.0 m$^2$/g |

TABLE II-continued

Properties Expected for an Example I Catalyst

| | |
|---|---|
| Pore Volume | 0.13 ml/g |
| Average Pore Diameter | 33.1 Å |

EXAMPLE 2

In experimental work, alkylation reactor runs would be carried out employing a single stage alkylation reactor. The reactor would be operated as a laboratory simulation of a single stage of a multiple stage reactor that would be used commercially. In carrying out the experimental work, a metal-promoted beta zeolite having a silica/alumina ratio of about 150 and a metal/aluminum atomic ratio of 0.75 would be employed. This catalyst would be formed employing a silica binder as described previously. Comparative experimental work carried out would use a lanthanum-promoted beta zeolite catalyst, also having a silica alumina ratio of 150 and having a lanthanum/aluminum atomic ratio of 1.0 formulated with a silica binder.

The metal-promoted beta zeolite would be used in the alkylation reactor through five (5) regenerations for a total cumulative time of in excess of 140 days. Throughout the successive runs the inlet temperature of the reactor would be about 300° C.±5° C. and the temperature at the outlet of the reactor would be about 350° C.±10° C., resulting in an incremental temperature increase across the reactor of about 40-50° C. The reactor would be operated at an inlet pressure of about 600 psig (4.1 MPa) with a pressure gradient across the reactor of only a few pounds per square inch. These conditions are more representative of near critical phase alkylation, but it should be understood that the catalysts can be employed in the liquid phase as well.

The lanthanum promoted zeolite beta would be employed in a test run spanning about 55 days on line with regeneration of the catalyst at the conclusion of 20 days. The lanthanum promoted zeolite beta may have a silica alumina ratio of 150 and a lanthanum/aluminum atomic ratio of 1.0. Generally, a regeneration procedure may involve injecting an oxygen-containing gas into the reaction zone to provide a regeneration temperature in the reaction zone of between about 500 and about 585° C.

EXAMPLE 3

This Example illustrates how use of dilute ethylene to alkylate benzene to ethylbenzene could be performed using mixed hexanes as the diluent for ethylene in place of ethane. The mixed hexanes did not undergo any substantial conversion in the reactor. The reaction could be run according to the conditions outlined in Table III

TABLE III

| | |
|---|---|
| Benzene:ethylene = molar | 10:1 molar |
| LHSV benzene | 10 hr$^{-1}$ |
| Ethylene rate | 83 ml/min STP |
| Pressure | 750 psig (5.2 MPa) |
| Feed | 12,500 g hexane |
| | 28,400 g benzene |
| Ethylene/diluent vol/vol | 20/80 |
| Diluent | Mixed hexanes |
| Temperature | 290° C. before ethylene addition |
| Catalyst volume | 20 ml |

Mixed hexanes may be used as a diluent in lieu of diluting ethylene with ethane. The hexanes were added as a mixture of branched isomers, many of which contained tertiary hydrogen that could react to create side products.

The test could be run for four days. After the first day, the ethylene may be added to the reactor. For this work, it is expected that all ethylene added to the reactor would consumed, and that there would be no gas in the effluent.

In such a test, as in all the experiments conducted in the critical phase, no xylenes would be expected to be produced. It would be expected that analysis by mass spec would show trace amounts of many different branched substituted benzene compounds in the effluent. These would be reported as unknowns/heavies. Since the heavies would be reported as ppm relative to ethylbenzene and there would be expected to result considerably more hexane than ethylbenzene in the effluent, only a small amount of isomers have to be converted to produce the heavies. These results would suggest that dilute ethylene could be used successfully to alkylate benzene to ethylbenzene. As such, it creates opportunities for obtaining alternate supplies of ethylene that could favor the use of critical phase technology economically. The results would also show that dilute benzene could be used as the substrate to perform the alkylation reaction.

It is expected that the ethyl benzene yield in terms of percent conversion, and that the by-product yield (e.g. propylbenzene and butylbenzene), relative to ethyl benzene, would be substantially better than the corresponding values observed for the lanthanum-promoted beta zeolite. This is because yttrium ion and the lanthanide ions are smaller and more electropositive than lanthanum, or cerium, for that matter. The metals of described herein would be expected to provide more selectivity and activity than lanthanum. As noted, generally the elements are more acidic and more electropositive going to the right on the Periodic Table from lanthanum.

The metal beta alkylation catalyst would be expected to show substantially lower by-products yield in each of the three (3) categories (propylbenzenes, butylbenzenes and heavies) as compared with lanthanum-promoted beta zeolite, and also as compared with cerium-promoted beta zeolite. Specifically, the composite by-product yield of propylbenzene and butylbenzene produced during super critical phase or liquid phase alkylation over the metal-promoted zeolite would be expected to be less than one-half of the corresponding by-product yield of propylbenzene and butylbenzene observed for the lanthanum-promoted zeolite. The data for the metal-promoted beta zeolites would be expected to show consistent results even after a series of regenerations.

Of course, the alkylation methods discussed herein are intended to be applied in a production-scale alkylation plant to produce large, commercial quantities of product, e.g. ethylbenzene.

In the foregoing specification, the catalysts and processes have been described with reference to specific embodiments thereof, and has been demonstrated as effective in providing methods for preparing alkylated aromatics, particularly ethylbenzene. However, it will be evident that various modifications and changes can be made to the method without departing from the broader spirit or scope of the innovations as set forth in the appended claims. Accordingly, the specification is to be regarded in an illustrative rather than a restrictive sense. For example, specific promoter-modified zeolites, aromatic compounds, alkylating agents, and other components falling within the claimed parameters, but not specifically identified or tried in a particular catalyst preparation method, are anticipated and expected to be within the scope of this invention.

Further, the process of producing alkylated aromatic products can be conducted under conditions (temperature, pressure, feed rates, etc.) other than those exemplified herein.

What is claimed is:

1. A process for alkylation of an aromatic compound comprising:
   supplying an aromatic feedstock comprising benzene into a reaction zone;
   contacting the aromatic feedstock with a metal-promoted zeolite beta molecular sieve alkylation catalyst in the reaction zone, wherein the metal-promoted zeolite molecular sieve alkylation catalyst comprises a first metal in an amount to provide a first metal/aluminum atomic ratio within a range of from about 0.1:1 to about 10:1, where the first metal is selected from the group consisting of yttrium, lanthanide series metals having an atomic number of at least 59 and combinations thereof and a second metal different from the first metal, the second metal is selected from the group consisting of yttrium, cerium, a rare earth of the lanthanide series other than lanthanum and combinations thereof,
   supplying ethylating agent to the reaction zone in an amount to provide an aromatic compound/alkylating agent mole ratio in the range of from about 1:1 to about 30:1 and wherein the alkylating agent comprises ethylene;
   operating the reaction zone at temperature and pressure conditions in which the aromatic compound is in the supercritical or liquid phase to cause alkylation of the aromatic compound in the presence of the zeolite alkylation catalyst to produce an alkylation product as a primary product with the attendant production of heavier alkylated by-products in a minor amount, wherein the primary product comprises ethylbenzene; and
   recovering the alkylation product from the reaction zone.

2. The process of claim 1, where the reaction zone is operated in supercritical phase and the benzene to ethylene mole ratio is less than about 10.

3. The process of claim 1, where the reaction zone is operated in liquid phase and the benzene to ethylene mole ratio is within the range of from about 1 to about 30.

4. The process of claim 1, wherein the zeolite has a silica/alumina mole ratio within the range of from about 50 to about 150.

5. The process of claim 1, wherein the alkylation zone is operated at temperature and pressure conditions to provide a composite by-product yield of propylbenzene and butylbenzene which is less than the corresponding composite by-product yield of propylbenzene and butylbenzene for a zeolite promoted with lanthanum at a lanthanum/aluminum atomic ratio at least equal to the metal/aluminum atomic ratio of the metal-promoted zeolite catalyst under the same temperature and pressure conditions.

6. The process of claim 1, wherein the alkylation reaction zone is operated at temperature and pressure conditions to provide a composite by-product yield of propylbenzene and butylbenzene which is no more than one-half of the corresponding by-product yield of propylbenzene and butylbenzene for a zeolite catalyst promoted with lanthanum at a lanthanum/aluminum atomic ratio at least equal to the metal/aluminum atomic ratio of the catalyst under the same temperature and pressure conditions.

7. The process of claim 1, further comprising terminating the supply of the aromatic feedstock and alkylating agent to the reaction zone and thereafter regenerating the metal-promoted zeolite in the reaction zone by a regeneration procedure comprising the injection of an oxygen-containing gas into the reaction zone to provide a regeneration temperature in the reaction zone of between about 500 and about 585° C. and thereafter reinstituting the supply of the aromatic feedstock and alkylating agent in the production of the alkylation product in accordance with claim 1.

* * * * *